(12) United States Patent
Nicholson et al.

(10) Patent No.: US 9,814,237 B2
(45) Date of Patent: Nov. 14, 2017

(54) USE OF 3-ISOXAZOLIDINONES AS SELECTIVE HERBICIDES IN GRASS AND BRASSICA CROPS

(75) Inventors: Paul Nicholson, Ewing, NJ (US); Sandra L. Shinn, Columbus, NJ (US); Robert F. Pepper, Bordentown, NJ (US); David A. Brain, Hillsborough, NJ (US)

(73) Assignee: FMC Corporation, Philadelphia, PA (US)

( * ) Notice: Subject to any disclaimer, the term of this patent is extended or adjusted under 35 U.S.C. 154(b) by 171 days.

(21) Appl. No.: 14/008,309

(22) PCT Filed: Apr. 12, 2012

(86) PCT No.: PCT/US2012/033253
§ 371 (c)(1),
(2), (4) Date: Sep. 27, 2013

(87) PCT Pub. No.: WO2012/148689
PCT Pub. Date: Nov. 1, 2012

(65) Prior Publication Data
US 2014/0045694 A1   Feb. 13, 2014

Related U.S. Application Data

(60) Provisional application No. 61/480,405, filed on Apr. 29, 2011.

(51) Int. Cl.
*A01N 43/80* (2006.01)
(52) U.S. Cl.
CPC .................. *A01N 43/80* (2013.01)

(58) Field of Classification Search
None
See application file for complete search history.

(56) References Cited

U.S. PATENT DOCUMENTS

| 4,405,357 A | 9/1983 | Chang |
| 4,692,182 A | 9/1987 | Chang |
| 4,826,527 A * | 5/1989 | Chang et al. ................. 504/271 |
| 4,892,578 A | 1/1990 | Chang et al. |
| 5,527,761 A | 6/1996 | Ensminger |
| 5,583,090 A | 12/1996 | Stern et al. |
| 5,597,780 A | 1/1997 | Lee et al. |
| 5,783,520 A | 7/1998 | Anderson et al. |
| 6,855,667 B2 * | 2/2005 | Keifer .......................... 504/103 |

FOREIGN PATENT DOCUMENTS

EP   0131765 A1   1/1985

OTHER PUBLICATIONS

Callihan et al. (Mustards in Mustards: Guide to Identification of Canola Mustard Rapeseed and Related Weeds. University of Idaho: Ag Communications; 2000).*

* cited by examiner

*Primary Examiner* — John Pak
*Assistant Examiner* — Jessica Kassa
(74) *Attorney, Agent, or Firm* — FMC Corporation

(57) ABSTRACT

The present invention is directed to the use of at least one 3-isoxazolidone herbicide selected from the group consisting of 2-(2,4-dichlorophenyl)methyl-4,4-dimethyl-3-isoxazolidone and 2-(2,5-dichlorophenyl)methyl-4,4-dimethyl-3-isoxazolidone as a selective herbicide in a grass or *brassica* crop selected from the group consisting of corn, rice, sorghum, barley, rye, and canola.

18 Claims, No Drawings

USE OF 3-ISOXAZOLIDINONES AS SELECTIVE HERBICIDES IN GRASS AND BRASSICA CROPS

This application claims the benefit of U.S. Provisional Application 61/480,405, filed Apr. 29, 2011.

FIELD OF THE INVENTION

The present invention is directed to the use of at least one 3-isoxazolidone herbicide selected from the group consisting of 2-(2,4-dichlorophenyl)methyl-4,4-dimethyl-3-isoxazolidone and 2-(2,5-dichlorophenyl)methyl-4,4-dimethyl-3-isoxazolidone as a selective herbicide in a grassy or *brassica* crop selected from the group consisting of corn, rice, sorghum, barley, rye, and canola/oilseed rape.

BACKGROUND OF THE INVENTION

The protection of crops from undesirable weeds which can interfere with crop growth has long been a goal in agriculture. One approach which has been taken to achieve this goal is the development of selective herbicides which can control weeds without exhibiting unacceptable phytotoxicity to the crops sought to be protected. More recently, crops have been protected from weeds by genetically modifying the crop to be resistant to a non-selective herbicide (such as glyphosate or glufosinate) and applying such herbicide over the top of such crops. Unfortunately, this latter approach has led to the development of herbicide tolerant weeds, with the result that there is still a need for a means of selectively controlling undesirable vegetation in fields.

U.S. Pat. No. 4,405,357 discloses certain 3-isoxazolidinones which exhibit desirable selective herbicidal activity. Specifically, such compounds are shown to be effective in controlling grassy and broadleaf species while leaving legumes, particularly soybeans, unaffected. Among the compounds specifically disclosed in this patent are 2-(2,4-dichlorophenyl)methyl-4,4-dimethyl-3-isoxazolidone (Compound 22) and 2-(2,5-dichlorophenyl)methyl-4,4-dimethyl-3-isoxazolidone (Compound 87). Both such compounds are demonstrated to be effective against a number of weeds; including, for one or both of such compounds, (a) monocot grasses such green foxtail, barnyard grass, goose grass, and crabgrass; and (b) dicot species such as chickweed, lambsquarters and velvetleaf.

It has now been discovered that despite such desirable activity, particularly on monocot grass species, both 2,4-Cl and 2,5-Cl may be employed as selective herbicides on grassy monocot crops including corn, rice, sorghum and sugarcane; as well as on the *brassica* species canola, without causing an undesirable amount of phytotoxicity to such crops. Moreover, such compounds exhibit reduced volatility relative to other 3-isoxazolidinone herbicides such as clomazone.

SUMMARY OF THE INVENTION

The present invention is directed to a method of selectively controlling undesirable vegetation in a grassy monocot or *brassica* crop selected from the group consisting of corn, rice, sorghum, sugarcane and canola (or oil seed rape) comprising applying an herbicidally effective amount of at least one 3-isoxazolidone herbicide selected from the group consisting of 2-(2,4-dichlorophenyl)methyl-4,4-dimethyl-3-isoxazolidone and 2-(2,5-dichlorophenyl)methyl-4,4-dimethyl-3-isoxazolidone to the locus of such vegetation.

DETAILED DESCRIPTION OF THE INVENTION

The present invention is directed to a method of selectively controlling undesirable vegetation in a grassy monocot or *brassica* crop selected from the group consisting of corn, rice, sorghum, sugarcane and canola (or oil seed rape) comprising applying an herbicidally effective amount of at least one 3-isoxazolidone herbicide selected from the group consisting of 2-(2,4-dichlorophenyl)methyl-4,4-dimethyl-3-isoxazolidone and 2-(2,5-dichlorophenyl)methyl-4,4-dimethyl-3-isoxazolidone to the locus of such vegetation.

As is employed herein, the term "herbicide" is used to denote a compound which controls or modifies the growth of plants. The term "herbicidally effective amount" is used to indicate the quantity of such compound which is capable of producing a controlling or modifying effect. Controlling or modifying effects include all deviations from natural development, for example: killing, retardation, leaf burn, albinism, dwarfing, and the like. The term "plants" refers to all physical parts of a plant, including seeds, seedlings, saplings, roots, tubers, stems, stalks, foliage, and fruits.

Both 2-(2,4-dichlorophenyl)methyl-4,4-dimethyl-3-isoxazolidone (hereinafter referred to as "2,4-Cl") and 2-(2,5-dichlorophenyl)methyl-4,4-dimethyl-3-isoxazolidone (hereinafter referred to as "2,5-Cl") are known compounds, and may be produced by processes such as those described in U.S. Pat. No. 4,405,357 (Chang).

Although 2,4-Cl and 2,5-Cl may be applied pre-emergently or post-emergently, it is preferred that they are employed pre-emergently. Such 3-isoxazolidinone compound is employed in an herbicidally effective amount. The amount constituting an effective amount is variable, depending on a number of factors such as the type of soil, the expected pattern of rainfall or irrigation, the plant species to be controlled, and the particular crop involved. Typically, between about 1 and about 4,000 grams of active ingredient per hectare is employed. Preferably, such compound is applied at a rate of between about 75 and 2,000 grams a.i./hectare; and more preferably at a rate of between about 125 and 1,500 grams a.i./hectare.

In the practice of the present invention, 2,4-Cl and/or 2,5-Cl are generally employed in the form of an agriculturally acceptable formulation comprising one or more adjuvants and/or carriers. Such herbicidal compositions typically comprise between about 0.01% and 95% active ingredient together with between about 4% and 98.5% agriculturally acceptable carrier and between about 1% and 15% surface active agent by weight. As is well-known in the art, the formulation and mode of application of a toxicant may affect the activity of the material in a given application. Thus, such active compounds may be formulated as an emulsifiable concentrate (EC), as a granule of relatively large particle size, as a wettable powder, as a solution, as a microcapsule, as a suspension concentrate (SC) or as any of several other known types of formulations, depending on the desired mode of application.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other non-volatile organic solvents. For example, a useful emulsifiable concentrate formulation, designated "4EC" because it contains four pounds of active ingredient per gallon of concentrate (0.479 kg/liter), contains 53 parts of 2,4-Cl and/or 2,5-Cl, 6.0 parts of a blend of alkylnaphthalenesulfonate and polyoxyethylene ethers as emulsifiers, 1.0 part of epoxidized soybean oil as stabilizer, and as solvent 40 parts of petroleum distillate having a high flash-point.

Granular formulations are particularly useful for aerial distribution. Useful granular formulations may be of several types Impregnated granules are those wherein the active ingredient is applied to large particles of an absorbent carrier, such as an attapulgite or kaolin clay, corncobs, expanded mica, normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for preemergence herbicides, are in the form of finely divided particles which disperse readily in water or other dispersants. The wettable powder is ultimately applied to the soil as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

2,4-Cl and 2,5-Cl may also be employed in the form of microencapsulated formulations, such as those described in U.S. Pat. Nos. 5,597,780, 5,583,090 and 5,783,520.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface active agents, many of which are available in commerce.

The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

In the practice of the present invention, 2,4-Cl and/or 2,5-Cl may be formulated and/or applied with other herbicides (so long as desirable selective control of weeds is maintained), insecticides, fungicides, nematicides, plant growth regulators, fertilizers, and other agricultural chemicals.

EXAMPLE 1

EC and SC Formulations of 2,4-Cl

Example 1A, EC

Into a two dram glass vial was placed 0.0227 gram of Niagara 1 surfactant, 0.159 gram of Niagara 2 surfactant (Niagara surfactants are available from Cognis), 0.045 gram of an alkyl EO/PO copolymer surfactant (Tergitol™ XD available from Dow® Chemical), 0.463 gram of 2,4-Cl and 1.3223 grams of a light aromatic solvent naphtha (Solvesso™ 100 Fluid available from ExxonMobil Chemical). The mixture was stirred and heated at 75° C. until all the ingredients melted. A homogenous amber liquid was obtained.

Example 1B, EC

Into a two dram glass vial was placed 0.0122 gram of Niagara 1 surfactant, 0.085 gram of Niagara 2 surfactant (Niagara surfactants are available from Cognis), 0.0242 gram of an alkyl EO/PO copolymer surfactant (Tergitol™ XD available from Dow® Chemical), 0.69 gram of 2,4-Cl and 0.705 gram of light aromatic solvent naphtha (Solvesso™ 100 Fluid available from ExxonMobil Chemical). The mixture was stirred and heated at 75° C. until all the ingredients melted. A homogenous amber liquid was obtained.

Example 1C, SC

In a one liter beaker, a mixture of 46.7 grams of water, 1.5 grams of an alkyl EO/PO copolymer surfactant (Tergitol™ XD available from Dow® Chemical), and 1.5 grams of an ethoxylated aliphatic alcohol phosphate ester, potassium salt (Ethox ERS 129 available from Ethox Chemicals) was stirred until all solid components had dissolved. Powdered 2,4-Cl (44.0 grams) was added and the resultant slurry was transferred to an attritor mill and was milled using 1 mm stainless steel balls until a particle size of less than 12 microns (D90, Malvern light scattering particle sizer) was achieved. The mixture was filtered through a 20 mesh screen to remove the milling balls. A mixture of 0.15 gram of a biocide (Proxel™ GXL Antimicrobial available from Arch® Biocides) 6.0 grams of propylene glycol and 0.15 gram of xanthan gum (Kelzan® M available from CPKelco) was added to the filtrate and stirred until homogenous.

EXAMPLE 2

EC Formulation of 2,5-Cl

A mixture of 45.45 grams of light aromatic solvent naphtha (Solvesso™ 100 Fluid available from ExxonMobil Chemical), 0.8 gram of Niagara 1 surfactant, 4.91 grams of Niagara 2 surfactant (Niagara surfactants are available from Cognis), 1.43 grams of an alkyl EO/PO copolymer surfactant (Tergitol™ XD available from Dow® Chemical) and 47.6 grams of 2,5-Cl was stirred until a homogenous solution was formed.

EXAMPLE 3

Pre-emergence Evaluation of 2,4-Cl and 2,5-Cl Formulations

The EC formulations of Examples 1 and 2 were diluted with distilled water and were applied pre-emergently using a DeVries sprayer at rates of 6.25, 125, 250, 375 and 500 grams of active ingredient/hectare (g ai/ha) to flats containing sandy loam soil planted with crop and weed seeds, three replicates for each rate. Crop seeds used in the evaluations were grassy monocots: rice (*Templeton variety*), corn (*Pioneer* 33M53 *variety*), sorghum (*Sorghum bicolor*), rye (*Lolium multiflorum*), barley (*Robust variety*) and brassica dicot; canola/oilseed rape (*Brassica napus*). Weed seeds included grasses such as barnyard grass (*Echinochloa crusgalli*), goose grass (*Eleusine indica*), crabgrass (*Digitaria horizontalis*) and green foxtail (*Setaria viridis*); and broadleaf weeds such as field chickweed (*Cerastium arvense*), lambquarters (*Chenopodium album*) and velvetleaf (*Abutilon theophrasti*). Untreated control flats and two commercial formulations of Clomazone (Clomazone 4EC Herbicide, a nonencapsulated emulsion concentrate formulation and Clomazone 3ME Herbicide, a microencapsulated formulation, both available from FMC Corporation) were included in each test. After application, the flats were placed in a greenhouse and watered regularly. Ratings are taken at 14 days after treatment (DAT). The trials were evaluated for percent weed control and crop injury (also listed as % control) based on visual observations compared to the untreated controls for each species.

Percent control was determined by a method similar to the 0 to 100 rating system disclosed in "Research Methods In Weed Science," 2nd ed., B. Truelove, Ed.; Southern Weed Science Society; Auburn University, Auburn, Ala., 1977. The present rating system is as follows:

| Rating Percent Control | Description of main Categories | Crop Description |
|---|---|---|
| 0 | No effect | No crop reduction or injury |
| 10 | Slight effect | Slight discoloration or stunting |
| 20 | | Some discoloration, stunting or stand loss |
| 30 | | Crop injury more pronounced but not lasting |
| 40 | Moderate effect | Moderate injury, crop usually recovers |
| 50 | | Crop injury more lasting, recovery doubtful |
| 60 | | Lasting crop injury, no recovery |
| 70 | Severe effect | Heavy injury and stand loss |
| 80 | | Crop nearly destroyed, a few survivors |
| 90 | | Only occasional plants left |
| 100 | Complete effect | Complete crop destruction |

The average of the results are summarized in Table 1, Tests 1 through 5 below, in which a number of crop and weed species were tested.

TABLE 1

Pre-emergence Control of Crops and Weeds 14 DAT

Test 1

| Test Formulation | Rate g ai/ha | % Control | | | |
|---|---|---|---|---|---|
| | | Rice | Crabgrass | Barnyard Grass | Goose grass |
| Control | | 0 | 0 | 0 | 0 |
| 4EC | 250 | 90 | 100 | 100 | 100 |
| | 125 | 58 | 100 | 86 | 91 |
| | 62.5 | 18 | 100 | 62 | 62 |
| 3ME | 250 | 73 | 100 | 94 | 100 |
| | 125 | 23 | 100 | 82 | 90 |
| | 62.5 | 6 | 88 | 43 | 57 |
| Example 1A | 250 | 55 | 100 | 100 | 100 |
| | 125 | 17 | 92 | 82 | 83 |
| | 62.5 | 5 | 62 | 65 | 82 |

Test 2

| Test Formulation | Rate g ai/ha | % Control | | | |
|---|---|---|---|---|---|
| | | Rice | Crabgrass | Barnyard grass | Goose grass |
| Control | | 0 | 0 | 0 | 0 |
| 4EC | 250 | 82 | 100 | 100 | 100 |
| | 125 | 43 | 100 | 100 | 98 |
| | 62.5 | 9 | 100 | 80 | 70 |
| 3ME | 250 | 55 | 100 | 95 | 100 |
| | 125 | 23 | 100 | 68 | 86 |
| | 62.5 | 7 | 97 | 47 | 45 |
| Example 2 | 250 | 6 | 97 | 84 | 53 |
| | 125 | 1 | 100 | 42 | 22 |
| | 62.5 | 0 | 78 | 23 | 5 |

TABLE 1-continued

Pre-emergence Control of Crops and Weeds 14 DAT

Test 3

| Test Formulation | Rate g ai/ha | % Control | | | | | | | |
|---|---|---|---|---|---|---|---|---|---|
| | | Rye | *Sorghum* | Canola | Lambs-quarter | Velvet-leaf | Barnyard grass | Green foxtail | Chick-weed |
| Control | | 0 | 0 | 0 | 0 | 0 | 0 | 0 | 0 |
| 4EC | 250 | 37 | 89 | 43 | 98 | 99 | 95 | 82 | 100 |
| | 125 | 28 | 62 | 31 | 100 | 90 | 77 | 60 | 100 |
| | 62.5 | 8 | 28 | 0 | 63 | 63 | 43 | 23 | 100 |
| 3ME | 250 | 33 | 68 | 33 | 97 | 97 | 78 | 58 | 100 |
| | 125 | 11 | 40 | 45 | 87 | 87 | 62 | 82 | 100 |
| | 62.5 | 6 | 22 | 0 | 43 | 43 | 38 | 15 | 100 |
| Example 1B | 250 | 30 | 43 | 1 | 34 | 34 | 100 | 76 | 100 |
| | 125 | 15 | 23 | 0 | 18 | 18 | 80 | 42 | 100 |
| | 62.5 | 6 | 9 | 0 | 7 | 7 | 52 | 18 | 100 |
| Example 2 | 250 | 17 | 47 | 0 | 22 | 22 | 60 | 28 | 100 |
| | 125 | 8 | 23 | 0 | 18 | 18 | 35 | 13 | 100 |
| | 62.5 | 2 | 7 | 0 | 3 | 3 | 20 | 3 | 90 |

Test 4

| Test Formulation | Rate g ai/ha | % Control | | | | | | |
|---|---|---|---|---|---|---|---|---|
| | | Rice | Corn | Chick-weed | Barnyard grass | Crab-grass | Green foxtail | Lambs-quarter |
| Control | | 0 | 0 | 10 | 0 | 0 | 0 | 0 |
| 4EC | 500 | 57 | 82 | 100 | 100 | 100 | 100 | 100 |
| | 375 | 68 | 85 | 100 | 100 | 100 | 100 | 100 |
| | 250 | 36 | 39 | 100 | 100 | 92 | 100 | 93 |
| | 125 | 12 | 12 | 100 | 86 | 52 | 95 | 85 |
| 3ME | 500 | 68 | 58 | 100 | 100 | 100 | 100 | 100 |
| | 375 | 30 | 48 | 100 | 99 | 93 | 97 | 100 |
| | 250 | 17 | 35 | 100 | 90 | 62 | 92 | 96 |
| | 125 | 6 | 2 | 100 | 69 | 20 | 71 | 72 |
| Example 1A | 500 | 32 | 27 | 100 | 100 | 100 | 100 | 78 |
| | 375 | 25 | 20 | 100 | 100 | 100 | 90 | 63 |
| | 250 | 10 | 9 | 100 | 100 | 100 | 96 | 40 |
| | 125 | 0 | 2 | 100 | 68 | 70 | 67 | 28 |
| Example 1C | 500 | 20 | 16 | 100 | 100 | 100 | 100 | 73 |
| | 375 | 23 | 18 | 100 | 100 | 100 | 100 | 62 |
| | 250 | 10 | 8 | 100 | 100 | 100 | 100 | 43 |
| | 125 | 1 | 0 | 100 | 68 | 47 | 62 | 16 |
| Example 2 | 500 | 3 | 9 | 100 | 84 | 99 | 92 | 37 |
| | 375 | 0 | 6 | 100 | 76 | 68 | 94 | 20 |
| | 250 | 0 | 2 | 100 | 65 | 30 | 68 | 9 |
| | 125 | 0 | 0 | 100 | 35 | 1 | 38 | 2 |

Test 5

| Test Formulation | Rate g ai/ha | % Control | |
|---|---|---|---|
| | | Barley | Canola |
| Control | | 0 | 0 |
| 4EC | 250 | 25 | 45 |
| | 125 | 7 | 5 |
| | 62.5 | 21 | 3 |
| 3ME | 250 | 3 | 19 |
| | 125 | 0 | 7 |
| | 62.5 | 0 | 3 |
| Example 1A | 250 | 0 | 3 |
| | 125 | 0 | 0 |
| | 62.5 | 0 | 0 |
| Example 2 | 250 | 3 | 0 |
| | 125 | 0 | 0 |
| | 62.5 | 0 | 0 |

EXAMPLE 4

Volatility Evaluation

Formulations of 2,4-Cl and 2,5-Cl were tested in a greenhouse to determine the amount of phytotoxic injury sustained by chickweed due to volatilization of the active ingredient from treated soil. Chickweed is very sensitive to clomazone and is a good indicator for bleaching compound volatility. Untreated control flats and two commercial formulations of Clomazone (Command® 4EC Herbicide, a non-encapsulated emulsion concentrate formulation and Command® 3ME Herbicide, a microencapsulated formulation, both available from FMC Corporation) were included in each test. These formulations are the reference standards against which the experimental formulations are compared. Four inch plastic pots were fitted with a basket style coffee filter, cut to size, placed in the bottom of each pot to cover the drainage holes and to stop soil from exiting the bottom of the pot. Each pot was filled with sandy loam soil that was sieved using a #10 mesh sieve to remove any large soil particles and debris. Filled soil pots were lightly watered prior to treatment application. The test solutions were applied to the soil surface using the DeVries Generation III sprayer, two replicates per test solution, at a rate of 0.25 g ai/ha.

Each replicate test was set-up by placing an empty four inch plastic pot onto a greenhouse bench. Pots containing mature chickweed, about 2 inches in height, were placed around the empty pot in an eight spoke pattern. Four pots of the mature chickweed were placed at the 3, 6, 9 and 12 o'clock positions of the spoke, while three pots were placed at the 1:30, 4:30, 7:30 and 10:30 o'clock positions of the spoke. Once all of the pots were in place, the empty four inch pot from each set-up was removed and a treated four inch soil pot was put in its place. The untreated chickweed plants were evaluated for phytotoxic injury at 14 days after treatment. Volatility was evaluated by measuring the distance (cm) from the center of the treated soil pot to the distal point where bleaching effects were observed on each spoke. All eight spokes for each treatment were evaluated. The amount of volatility was determined by calculating the total square centimeters of phytotoxic injury per treatment. Command® 4EC was considered to have zero volatility control as this formulation consists of 100% free clomazone. The volatility reported is relative to the Command® 4EC values which were normalized to 100%. Table 2 below summarizes the average of the volatility evaluations.

TABLE 2

Volatility Evaluations

| Test Formulation | Rate of Application g ai/ha | % Volatility Compared to Command ® 4EC |
| --- | --- | --- |
| Control | 0 | 0 |
| Command ® 4EC | 250 | 100 |
| Command ® 3ME | 250 | 21.5 |
| Example 1A | 250 | 31.0 |
| Example 2 | 250 | 48.8 |

It was found that there was significant control of volatility of formulations containing non-encapsulated 2,4-Cl and 2,5-Cl compounds when compared to the non-encapsulated clomazone formulation.

What is claimed is:

1. A method of selectively controlling undesirable vegetation in a grassy monocot or brassica crop selected from the group consisting of corn, rice, barley and canola, the method comprising applying a selectively herbicidally effective amount of at least one 3-isoxazolidinone herbicide selected from the group consisting of 2-(2,4-dichlorophenyl)methyl-4,4-dimethyl-3-isoxazolidinone and 2-(2,5-dichlorophenyl)methyl-4,4-dimethyl-3-isoxazolidinone to the locus of such vegetation in said crop, wherein said selectively herbicidally effective amount is (1) an amount that is effective for selectively controlling the undesirable vegetation and (2) an amount that does not cause an undesirable amount of phytotoxicity to said crop even in the absence of other agricultural chemicals.

2. The method of claim 1 wherein such herbicide is employed pre-emergently.

3. The method of claim 2 wherein the herbicide is 2-(2,4-dichlorophenyl)methyl-4,4-dimethyl-3-isoxazolidinone.

4. The method of claim 3 wherein the herbicide is employed at a rate of between about 1 and about 4000 grams of active ingredient/hectare.

5. The method of claim 4 wherein the herbicide is employed at a rate of between about 75 and about 2,000 grams of active ingredient/hectare.

6. The method of claim 5 wherein the herbicide is employed at a rate of between about 100 and about 1,500 grams of active ingredient/hectare.

7. The method of claim 3 wherein the crop is a grassy monocot.

8. The method of claim 7 wherein the crop is corn, rice, or barley.

9. The method of claim 3 wherein the crop is a *brassica dicot*.

10. The method of claim 9 wherein the crop is canola.

11. The method of claim 2 wherein the herbicide is 2-(2,5-dichlorophenyl)methyl-4,4-dimethyl-3-isoxazolidinone.

12. The method of claim 11 wherein the herbicide is employed at a rate of between about 1 and about 4000 grams of active ingredient/hectare.

13. The method of claim 12 wherein the herbicide is employed at a rate of between about 75 and about 2,000 grams of active ingredient/hectare.

14. The method of claim 13 wherein the herbicide is employed at a rate of between about 100 and about 1,500 grams of active ingredient/hectare.

15. The method of claim 11 wherein the crop is a grassy monocot.

16. The method of claim 15 wherein the crop is corn, rice, or barley.

17. The method of claim 11 wherein the crop is a *brassica dicot*.

18. The method of claim 17 wherein the crop is canola.

* * * * *